US011094283B2

(12) United States Patent
Saur et al.

(10) Patent No.: US 11,094,283 B2
(45) Date of Patent: Aug. 17, 2021

(54) HEAD-WEARABLE PRESENTATION APPARATUS, METHOD FOR OPERATING THE SAME, AND MEDICAL-OPTICAL OBSERVATION SYSTEM

(71) Applicant: Carl Zeiss Meditec AG, Jena (DE)

(72) Inventors: Stefan Saur, Aalen (DE); Marco Wilzbach, Stuttgart (DE); Christopher Käsbach, Aalen (DE)

(73) Assignee: CARL ZEISS MEDITEC AG, Jena (DE)

(*) Notice: Subject to any disclaimer, the term of this patent is extended or adjusted under 35 U.S.C. 154(b) by 0 days.

(21) Appl. No.: 15/957,291

(22) Filed: Apr. 19, 2018

(65) Prior Publication Data
US 2018/0308451 A1 Oct. 25, 2018

(30) Foreign Application Priority Data
Apr. 21, 2017 (DE) .................. 10 2017 108 551.3

(51) Int. Cl.
*G09G 5/02* (2006.01)
*G09G 3/00* (2006.01)
(Continued)

(52) U.S. Cl.
CPC ........... *G09G 5/02* (2013.01); *G02B 27/0172* (2013.01); *G02B 27/0179* (2013.01); *G06F 3/012* (2013.01); *G06F 3/013* (2013.01); *G09G 3/002* (2013.01); *G09G 5/14* (2013.01); *G16H 30/20* (2018.01); *G16H 40/63* (2018.01); *G02B 2027/014* (2013.01); *G02B 2027/0118* (2013.01); *G02B 2027/0138* (2013.01);
(Continued)

(58) Field of Classification Search
CPC ...... G09G 5/02; G09G 3/002; G09G 2354/00; G02B 2027/0178; G06F 1/163; G06F 3/0304; G06F 1/1686; G06F 3/011
See application file for complete search history.

(56) References Cited

U.S. PATENT DOCUMENTS 9,293,118 B2 * 3/2016 Matsui ................. G09G 5/377
2012/0086624 A1 4/2012 Thompson et al.
(Continued)

FOREIGN PATENT DOCUMENTS

DE 103 35 369 3/2005
WO WO-2014/197337 12/2014
(Continued)

OTHER PUBLICATIONS

German Office Action for 10 2017 108 551.3 dated Sep. 20, 2017.

*Primary Examiner* — Samantha (Yuehan) Wang
(74) *Attorney, Agent, or Firm* — Nixon Peabody LLP; Jeffrey L. Costellia (57) ABSTRACT

A method for operating a head-wearable presentation apparatus is provided. The method comprises the steps of: capturing data that are representative of at least one state variable of the head of a person wearing the head-wearable presentation apparatus, evaluating the captured data in order to determine the at least one state variable of the head, and modifying a degree of transparency of at least one playback arrangement of the head-wearable presentation apparatus if the at least one state variable of the head corresponds to a predetermined state variable.

17 Claims, 3 Drawing Sheets

(51) Int. Cl.
*G16H 40/63* (2018.01)
*G16H 30/20* (2018.01)
*G02B 27/01* (2006.01)
*G06F 3/01* (2006.01)
*G09G 5/14* (2006.01)

(52) U.S. Cl.
CPC .............. *G02B 2027/0178* (2013.01); *G02B 2027/0187* (2013.01); *G09G 2354/00* (2013.01)

(56) References Cited

U.S. PATENT DOCUMENTS

2013/0265330 A1* 10/2013 Goto .................. G02B 27/0172
  345/632
2015/0173846 A1* 6/2015 Schneider .......... A61B 1/00009
  600/424
2016/0377863 A1 12/2016 Eromäki
2018/0204380 A1* 7/2018 Kumar .................... G06T 19/20
2018/0302557 A1* 10/2018 Rogers ............. H04N 21/23439

FOREIGN PATENT DOCUMENTS

WO   WO-2014197337 A1 * 12/2014 ........... A63F 13/213
WO   WO-2016/142263      9/2016

\* cited by examiner

HEAD-WEARABLE PRESENTATION APPARATUS, METHOD FOR OPERATING THE SAME, AND MEDICAL-OPTICAL OBSERVATION SYSTEM

CROSS-REFERENCE TO RELATED APPLICATION

The present application claims priority to German Application No. 10 2017 108 551.3 filed Apr. 21, 2017, the disclosure of which is hereby incorporated by reference herein in its entirety.

BACKGROUND OF THE INVENTION

Field of the Invention

The invention relates to a method for operating a head-wearable presentation apparatus such as a head-mounted display, for example. Further, the invention relates to a computer program product for carrying out such a method, to a head-wearable presentation apparatus, and to a medical-optical observation system having a head-wearable presentation apparatus.

Description of Related Art

Currently, the microsurgery market is undergoing the transformation of digitization. Driven by ergonomic advantages and electronic image improvement/augmentation and ever newer digital imaging and intraoperative methods, a 2-D or 3-D monitor is ever more frequently used as a primary image source. However, these methods also have technical disadvantages such as, for example, distance-dependent depth impressions, a viewing-angle-dependent color reproduction, greater demands for area in the operating theater, lines as tripping hazards and hygienic challenges within the scope of cleaning. Therefore, the use of HMD systems (head-mounted display systems) in the medium-term to long-term is becoming apparent.

For the use of such an HMD system in microsurgery, flexible switching between augmented reality, virtual-reality, and a "clear" view for a surgeon is desirable so that, depending on the situation, the advantages of the respective mode can be used to be able to carry out the surgeon's work efficiently, effectively and safely.

Virtual reality (VR) offers the advantage of complete immersion. The surgeon is not distracted by the surroundings and a high contrast presentation of information items (e.g. image data from a digital surgical microscope or from pre-surgery radiology data), for example, is possible as the ambient light has no influence. However, the surgeon simultaneously loses the reference to his surroundings: actions in his surroundings can no longer be perceived visually. The surroundings may possibly need to be captured by additional cameras and superimposed (so-called VR see-through); however, this represents a restricted view (latencies, color presentation, resolution etc.) of the real surroundings since the surgeon may, if need be, have to move the cameras in order to be able to perceive his surroundings as desired. Furthermore, when the surgeon wears VR goggles, it is not possible either to observe persons or appliances in the room in a targeted manner in order to read further information items or interact therewith.

Immersion is not possible in the case of augmented reality (AR) systems; that is to say, important information items such as, for instance, image data can only be presented poorly in certain circumstances, for example due to a contrast that is too low, because the ambient illumination has a direct influence. Further, the surgeon can be distracted more easily by his surroundings when a work step has to be carried out with high concentration (example: a surgeon placing a clip for treating an aneurysm). However, AR systems are advantageous in that the surgeon can continue to perceive his surroundings as usual (also referred to as peripheral vision). By way of example, an AR display in the form of stereo spectacles is described in DE 103 35 369 A1. Using this AR display, it is possible to display virtual buttons in such a way that they can only be seen by observers if they look in a certain direction, and so the virtual buttons appear as fixed in real space.

During the course of a surgical intervention, there are various phases with different requirements on a visualization system. When using a digital surgical microscope, which is usually used in difficult work steps, a VR system would be advantageous for the surgeon so as to be able to fully concentrate on the task at hand. In other phases, such as e.g. at the start of a surgical intervention, an AR system would be advantageous for the surgeon in order, for example, to be able to see the outlines of a craniotomy directly on the patient head or to have the radiological data of the spinal column of the patient visualized on the patient's back so that the correct region of the patient's back can be exposed. During an operation, it is particularly important for the surgeon to be able to continuously interact with the theater nurse or the surroundings, for example to receive or dispose of instruments or to be able to reposition an appliance. To this end, the surgeon requires a "clear view" without impairments.

It would be possible to make the degree of transparency of the display dependent on the position on the display. By way of example, a display could be opaque in the upper region and transparent in the lower region, for example, and so an oblique downward view with high transparency is possible, for instance in order still to be able to recognize the hands and/or surgical instruments. However, in the case of looking straight ahead, the gaze would be directed at the opaque upper region of the display, i.e. on the region with a degree of transparency of 0%, which would act as a pure VR region.

However, it would be more advantageous to be able to switch between clear view, AR, and VR, depending on the situation. In order to use the advantages of both AR systems and VR systems, it is possible to equip AR goggles with displays, the degree of transparency of which can be set between 0% (opaque) and 100% (transparent). Such an apparatus is known from US 2012/0086624 A1, for example. This allows a user to be able to switch between the VR, AR, and no-AR ("clear view"), depending on the situation. However, switching between the settings of the degree of transparency requires an interaction by the wearer by means of a keyboard, a mouse, a joystick or the like. The aforementioned solution is therefore disadvantageous in that it would interrupt the workflow of the physician carrying out the operation (e.g. a surgeon), since surgical instruments would have to be removed from the site or even deposited for the purposes of operating the keyboard, the mouse, the joystick, etc. Firstly, an interruption of the workflow can lead to higher risk for the patient (longer operating time, sterility, etc.).

SUMMARY OF THE INVENTION

With reference to the aforementioned prior art, it is an object of the present invention to provide an advantageous method for operating a head-wearable presentation apparatus, in particular a head-mounted display, and a corresponding computer program product. It is a further object of the present invention to provide a head-wearable presentation apparatus that can be operated easily without interrupting the workflow.

The first object is achieved by a method as claimed in claim 1 and by a computer program product as claimed in claim 7. The second object is achieved by a presentation apparatus as claimed in claim 8. The dependent claims contain advantageous embodiments of the invention.

In the method according to the invention for operating a head-wearable presentation apparatus, the following steps are carried out:

a. capturing data that are representative of at least one state variable of the head of a person wearing the head-wearable presentation apparatus, b. evaluating the captured data in order to determine the at least one state variable of the head, and c. modifying a degree of transparency of at least one playback arrangement of the head-wearable presentation apparatus if the determined at least one state variable of the head corresponds to a predetermined state variable.

The head-wearable presentation apparatus, which may be fixed to the head by means of a head sidepiece or a headband, for example, may be embodied as a head-mounted display. Here, a head-mounted display (also referred to as HMD) is understood to be a visual output appliance that is worn on the head. It presents images on a display of the playback arrangement. By way of example, the display can be a display arranged in front of the eyes, the degree of transparency of which for optical signals can be modified by applying a voltage, for example, and the image of which can be observed by means of suitable optics arranged between the display and the eye. By way of example, such a display can be produced by means of LCD shutter technology. Alternatively, use can be made of a conventional display, the image content of which can be reflected to the eye via a reflection area, the degree of transparency of which for optical signals can be modified by applying a voltage, for example. In a further alternative, use can be made of a conventional display, the image content of which is reflected to the eye via a conventional beam splitter, with the beam splitter then having assigned a device that allows the intensity of ambient light incident on the beam splitter to be reduced. Here, the head-mounted display may also have respectively one display with a variable degree of transparency for the right eye and the left eye, respectively one conventional display together with a reflection area with a variable degree of transparency or respectively one conventional display together with respectively one conventional beam splitter and a device for reducing ambient light that is incident on the beam splitter or beam splitters, wherein the degree of transparency of the display, of the reflection area or of the device for reducing ambient light that is incident on the beam splitter can be set, preferably independently, for the right and the left eye. The degree of transparency of the display, of the reflection area or of the device for reducing ambient light that is incident on the beam splitter can be set, in particular, in a range from 0% (opaque) to 100% (transparent) as desired. Holographic displays can also find use as displays in the head-wearable presentation apparatus.

As an alternative to the use of physical displays, there is also the option of using virtual displays in the head-wearable presentation apparatus. In the case of a virtual display, an image is projected directly onto the retina. Then, in addition to at least one virtual display, the head-wearable presentation apparatus comprises a device for reducing ambient light that reaches the eyes, with the degree of the reduction in ambient light that reaches the eyes being adjustable. Here, the degree of transparency of the device for reducing ambient light that reaches the eyes can be set, preferably, in a range from 0% (opaque) to 100% (transparent) as desired.

However, the head-wearable presentation apparatus may also be a loupe. In this case, the playback arrangement may comprise a beam splitter, by means of which an image can be superimposed into the beam path of the loupe and the transparency of which can be modified, in particular in the range from 100% transparent to 0% transparent. However, as in the case of the head-mounted display, there is also the option of using a conventional beam splitter together with a device that can be used to reduce the intensity of ambient light that is incident on the beam splitter.

The at least one state variable of the head represented by the captured data may contain the viewing direction of the head of the person wearing the head-wearable presentation apparatus. Here, the viewing direction should not be considered to be the position of the eyes but the orientation of the head, with the assumption being made that the eyes look straight ahead. In this case, the captured data are orientation data which reflect the orientation of the head of the user. In addition to the orientation data, it is also possible to capture position data of the head of the person wearing the head-wearable presentation apparatus as data that are representative of at least one state variable of the head. Then, in addition to the viewing direction, the at least one state variable of the head also contains the position of the head of the person wearing the head-wearable presentation apparatus. Thus, it is possible to ascertain not only the viewing direction but also the viewing direction proceeding from a certain position in space.

If it is not only the position of the head-wearable presentation apparatus but also the position of the patient that is captured, it is possible to ascertain the relative orientation between patient or operating site on the one hand and the presentation apparatus on the other hand, and so the position of the patient or the operating site can be ascertained in the coordinate system of the presentation apparatus and, for example, a live image of a digital operating microscope can always be displayed if the surgeon looks at the operating site. If, moreover, the positions of appliances such as the operating microscope, for example, are captured, the information items about these positions can be used to switch the head-wearable presentation apparatus into the AR mode, for example, when looking in the direction of one of the appliances and to display a user interface of the appliance when the surgeon looks at the appliance.

Thus, a viewing-direction-dependent control of the head-wearable presentation apparatus can be achieved using the method according to the invention by way of the comparison between the determined viewing direction and a predetermined direction. Thus, the head-wearable presentation apparatus can be operated easily and intuitively without interrupting the workflow.

In a special configuration of the method according to the invention, reference data for the data representing the at least one state variable of the head can be captured by targeting a reference point. By way of example, a screen, an IR beacon or any other marker, such as, for example, a marker pointing in the direction of the patient, can be used as a reference point. Targeting the reference point then sets the reference data for the at least one state variable of the head. Consequently, it is possible to provide an information item about the relative position between a coordinate system assigned to the reference point and a coordinate system assigned to the head-wearable presentation apparatus. This allows the orientation of the head-wearable presentation apparatus to be newly ascertained in relation to a predetermined reference coordinate system on the basis of the reference data, for example after repositioning of the surgeon.

According to an alternative embodiment variant of the method according to the invention, the data that are representative of the at least one state variable of the head contain movement data and/or acceleration data of the head-wearable presentation apparatus and the at least one state variable of the head contains a head movement of the person wearing the head-wearable presentation apparatus. Thus, for example, it is possible to deactivate the VR mode by shaking the head as a predetermined state variable of the head and activate said VR mode by nodding as another predetermined state variable of the head, or vice versa.

According to another alternative embodiment variant of the method according to the invention, image data are captured, by means of at least one camera assigned to the head-wearable presentation apparatus, in particular by at least one camera that is arranged at the head-wearable presentation apparatus or that is worn on the head, as data that are representative of the at least one state variable. Once again, the at least one state variable of the head contains the viewing direction of the person wearing the head-wearable presentation apparatus. For the purposes of determining the viewing direction, the image data are evaluated in order to determine a predetermined image content and, if the predetermined image content is present, a predetermined viewing direction is deduced as a predetermined state variable of the head. Here, predetermined image contents may be certain objects in the region of the user wearing the head-wearable presentation apparatus that can be recognized again within the scope of the evaluation. By way of example, if the surgeon looks at a suitably positioned ground glass screen, the latter and the corresponding viewing direction are identified within the evaluation and the site is superimposed in the VR mode. By way of example, other objects can be appliances. If the latter are recognized in the viewing direction of the surgeon, it is possible to switch over into the AR mode, for example, so that the operating elements thereof, for example, are identifiable. However, the image data can also find use in creating a map of the surroundings, in which the orientation and position of the head of the person (O) wearing the head-wearable presentation apparatus—and hence their viewing direction—are known. In addition to grayscale values or color values for the individual pixels, the image data may also contain distance values assigned to the pixels, said distance values specifying the distance from a certain point. Such distance data can be obtained by means of stereo cameras or by means of TOF cameras (TOF: time of flight). In order to create the map of the surroundings, use can be made of different approaches, for example a so-called SLAM approach, where SLAM denotes "Simultaneous Localization and Mapping". In the SLAM approach, a map of the surroundings is created incrementally from recordings of the surroundings of the camera fastened to the presentation apparatus, the position and orientation of the head-mounted display—and hence of the head of the wearer of the head-wearable presentation apparatus—being known in said map. Then, the viewing direction of the wearer emerges from the orientation of the head.

The aforementioned embodiment variants of the method according to the invention may find use individually or in combination. Thus, it is possible to increase the number of controllable actions, for example, if both the viewing direction and the head movement are ascertained as state variables of the head.

Further, the invention includes a computer program product with program code for carrying out the method according to the invention when the program code is loaded onto a computer and/or executed on a computer.

Moreover, according to the invention, a head-wearable presentation apparatus is provided for carrying out the method according to the invention. Said apparatus comprises a. a capturing unit with means for capturing data that are representative of at least one state variable of the head of a person wearing the head-wearable presentation apparatus,
b. an evaluation unit for evaluating the captured data in order to determine the at least one state variable of the head therefrom, and
c. an actuation unit for modifying a degree of transparency of at least one playback arrangement of the head-wearable presentation apparatus if the at least one state variable of the head corresponds to a predetermined state variable.

The data that are representative of at least one state variable of the head can represent orientation data, wherein the at least one state variable of the head then contains the viewing direction of the person wearing the head-wearable presentation apparatus. Here, the viewing direction should not be considered to be the position of the eyes but the orientation of the head, with the assumption being made that the eyes look straight ahead. In addition to the orientation data, the data that are representative of at least one state variable of the head can also represent position data of the head-wearable presentation apparatus. In this case, in addition to the viewing direction, the at least one state variable of the head also contains the position of the head of the person wearing the head-wearable presentation apparatus. Moreover, there may be a reference point for capturing reference data for the data representing the at least one state variable of the head.

Additionally, or alternatively, the data that are representative of at least one state variable of the head may contain movement data and/or acceleration data of the head. Then, the at least one state variable of the head contains a head movement of the person wearing the head-wearable presentation apparatus.

The evaluation unit and/or the actuation unit can be integrated into the head-wearable presentation apparatus or realized as software on a computer.

Means for capturing the orientation of the head or the movement of the head of a wearer of the head-wearable presentation apparatus are, for instance, acceleration sensors, position sensors (e.g. gyroscopes), markers for capturing the orientation and/or the position of the head by means of a position capturing system, etc.

Further additionally, or alternatively, the head-wearable presentation apparatus can be embodied to capture, using a camera that is arranged at the head-wearable presentation apparatus or a camera that is wearable on the head, image data as data that are representative of the at least one state variable of the head, with the at least one state variable of the head containing the viewing direction of the person wearing the head-wearable presentation apparatus, and to evaluate the image data so as to determine the viewing direction in order to determine the image content and to deduce a predetermined viewing direction if a predetermined image content is present.

Possible configurations of the head-wearable presentation apparatus as a head-mounted display or as a loupe were already described with reference to the method according to the invention. Reference is made to this description.

The advantages that are obtainable by the head-wearable presentation apparatus according to the invention emerge immediately from the advantages described with reference to the method according to the invention.

According to the present invention, a medical-optical observation system having a medical-optical observation appliance and a head-wearable presentation apparatus according to the invention are moreover provided. Here, the one medical-optical observation appliance can be an operating microscope, for example, which records object images by means of the image sensors, said object images then being transmitted to the head-wearable presentation apparatus in order to be presented in a suitable manner if the at least one state variable of the head corresponds to a certain state variable. By way of example, the image recorded using the medical-optical observation appliance can be displayed as a VR image in the head-wearable presentation apparatus if the state variable signals a look in the direction of the operating site or a certain head movement. However, the medical-optical observation appliance can also simply be a camera, the images of which are transmitted to the head-wearable presentation apparatus in order to be displayed, for example, if the wearer of the presentation apparatus looks in a certain direction or carries out a certain head movement. Further, it is possible for the medical-optical observation appliance to be an endoscope or endomicroscope equipped with at least one image sensor, the images of which are transmitted to the head-wearable presentation apparatus in order to be displayed, for example, if the wearer of the presentation apparatus looks in a certain direction or carries out a certain head movement.

Further features, properties and advantages of the present invention will become apparent from the following description of exemplary embodiments with reference to the accompanying figures.

DETAILED DESCRIPTION OF THE INVENTION

Figure 1:
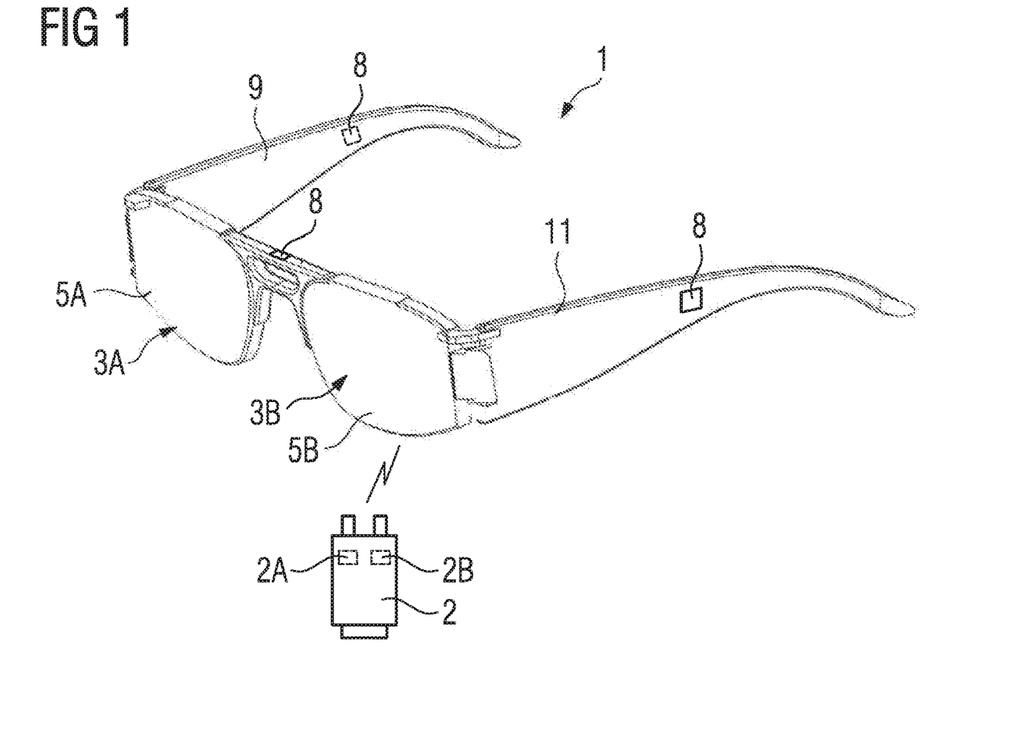
FIG. 1 shows a head-mounted display as an exemplary embodiment of a head-wearable presentation apparatus, together with an operating microscope.

Reference is initially made to FIG. 1. A head-wearable presentation apparatus is illustrated therein, said head-wearable presentation apparatus being embodied as a head-mounted display 1 in the present exemplary embodiment. In the present exemplary embodiment, the head-mounted display 1 acts both as VR goggles and as AR goggles. In the present exemplary embodiment, the head-mounted display 1 receives, in wireless fashion, images from image sensors 2A, 2B of a medical-optical observation appliance, namely an operating microscope 2, said images being presented as VR images or AR images using the head-mounted display 1 if certain state variables of the head-mounted display 1 are present. However, additionally, or alternatively, the head-mounted display 1 may also receive images from other sources, in particular from other medical-optical observation appliances, and may present said images as VR images or AR images if certain state variables of the head-mounted display 1 are present. Possible other sources are conventional cameras, endoscopes, endomicroscopes, image storage with pre-surgical data or images containing patient data, etc.

The head-mounted display 1 has, for each eye, respectively one playback arrangement 3A, 3B with a display 5A, 5B and head sidepieces 4. Using the head sidepieces 4, the head-mounted display 1 can be fastened and worn on the head 13 of the wearer of the head-mounted display 1, a surgeon O (see FIG. 4) in the present exemplary embodiment. Image data playback can be effectuated using the two displays 5A, 5B, within the scope of which image data are imaged into the visual field of the surgeon O. The displays 5A, 5B are assigned to respectively one eye of the surgeon O and can be actuated differently in order also to be able to provide 3-D image data in a spatial fashion, i.e. with depth perception. LCD displays with LCD shutter technology are used as displays 5A, 5B in the present exemplary embodiment. The LCD shutter technology renders it possible to set the degree of transparency of the LCD displays as desired between 0% (opaque) and 100% (transparent) by applying a control voltage.

Figure 2:
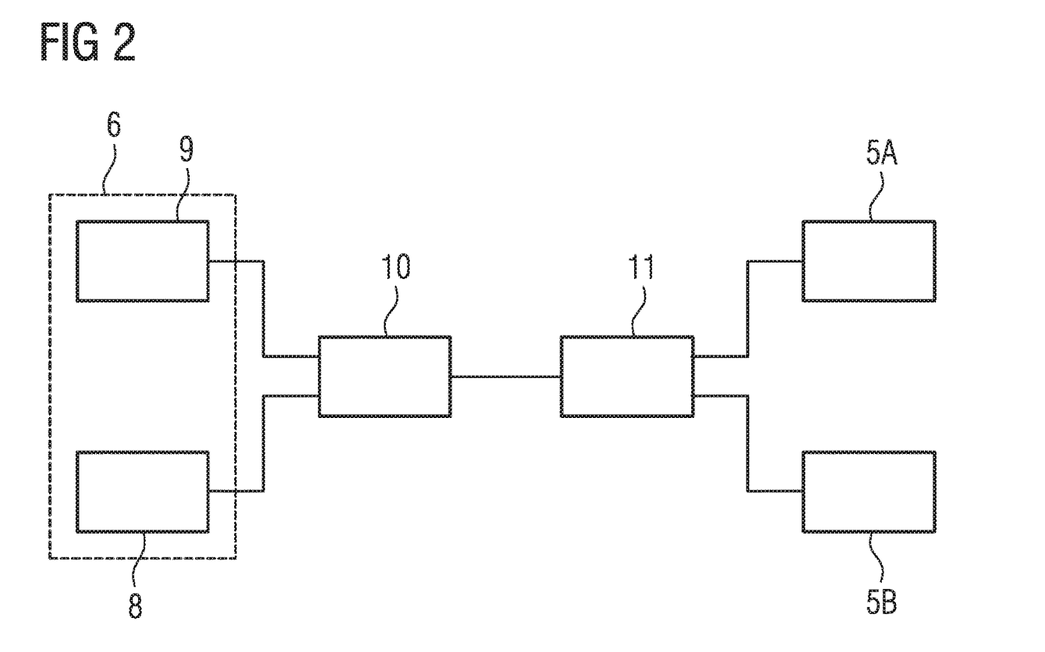
FIG. 2 shows a schematic illustration of components of the head-mounted display shown in FIG. 1.

Now, further components of the head-mounted display 1 are described with additional reference to FIG. 2. In the present exemplary embodiment, these are a capture unit 6, an evaluation unit 10 and an actuation unit 11.

Figure 4:
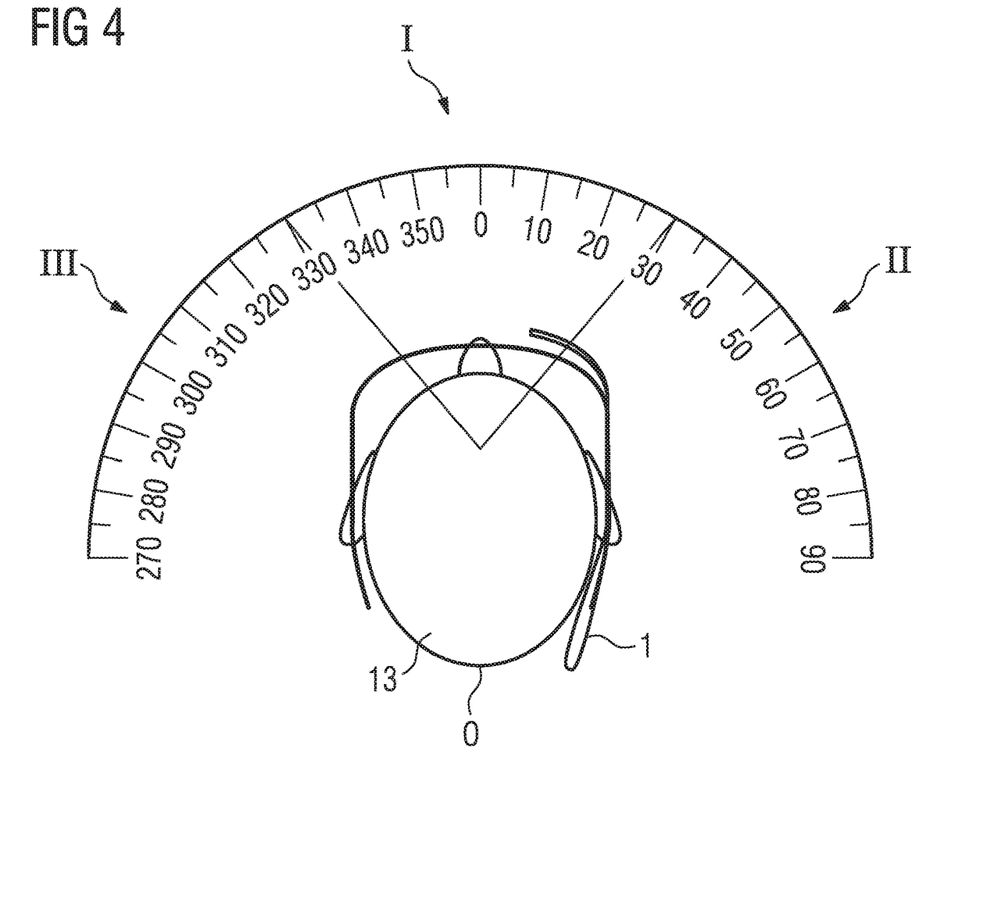
FIG. 4 shows the head-mounted display shown in FIG. 1 in operation.

The capture unit 6 is embodied to capture data D that are representative of a state variable of the head 13 of the surgeon O (see FIG. 4). In the present exemplary embodiment, orientation data, for example in the form of angle values, which describe the orientation of the head 13 of the surgeon O (e.g. azimuth angle and polar angle) are captured as data. To this end, use is made in the present exemplary embodiment of three markers 8 that are arranged on the head-mounted display 1, the positions of said markers being continuously captured by means of a tracking system (not illustrated here). Only two markers are used in other variants. In principle, these are sufficient for ascertaining the azimuth angle and the polar angle. Using three markers 8, it is still additionally possible to capture a head rotation about the viewing direction. Then, it is possible to ascertain the orientation of the head-mounted display 1, and hence the orientation of the head 13, from the captured position of the three markers 8.

As an alternative to the described ascertainment of the orientation data on the basis of the markers 8, the orientation data can also be captured by means of a gyroscopic sensor that is arranged at the head-mounted display 1.

In the present exemplary embodiment, an acceleration sensor 9 is also arranged at the head-mounted display 1 in addition to the markers 8. Using the acceleration sensor 9, it is possible to capture head movements such as a shaking of the head or a nodding of the head, for example, as further state variables of the head 13.

The orientation data of the head-mounted display 1 are indicative of the viewing direction of the surgeon O wearing the head-mounted display 1 on his head 13, whose eyes are directed straight ahead. In the present exemplary embodiment, the evaluation unit 10 is embodied to evaluate the captured orientation data D in order to determine the viewing direction of the surgeon O under the assumption of looking straight ahead.

Additionally, the evaluation unit 10 is embodied in the present exemplary embodiment to capture head movements on the basis of the acceleration data captured by the acceleration sensor 9 and to compare said head movements with certain predetermined head movements in order to determine whether the surgeon O shakes his head 13 or nods his head 13.

The actuation unit 11 is embodied to modify the degree of transparency of the displays 5A, 5B of the head-mounted display 1 upon reception of a signal S that was provided by the evaluation unit 10 and indicates the viewing direction of the surgeon, or optionally a shaking or nodding of the head, should the viewing direction be in a predetermined direction. By modifying the degree of transparency of the displays 5A, 5B depending on the ascertained viewing direction (established from the orientation of the head 13 and the assumption of eyes looking straight ahead) or optionally depending on a shaking or nodding of the head, an intuitive control of the head-mounted display 1 is facilitated for the situation-dependent switch-over between various modes such as clear view, AR and/or VR, for example. Examples of such modes include:

a. no transparency of the displays 5A, 5B in the case of a centrally forward viewing direction with a presentation of the live image of an operating microscope as a VR presentation;

b. complete transparency in the lower region of the displays 5A, 5B when viewing downward in the forward direction in order to be able to see instruments;

c. complete transparency of the displays 5A, 5B in the case of a viewing direction to the right in order to be able to interact with the theater nurse and/or an AR presentation of pre-surgical data, for example radiological 3-D data;

d. complete transparency of the displays 5A, 5B in the case of the viewing direction to the left in order to be able to interact with visitors and/or an AR presentation of patient data such as e.g. pulse, oxygen saturation, etc.;

e. complete transparency of the displays 5A, 5B independently of the viewing direction when shaking the head;

f. no transparency of the displays 5A, 5B independently of the viewing direction when nodding the head.

The listed examples are not exhaustive and should only indicate the possibilities of the invention.

The modes assigned to the viewing directions and/or head movements and/or possible other state variables of the head 13 can be stored for a surgeon in a configuration profile. Then, the configuration profile stores what transparency setting should apply for which state variable of the head 13, i.e. at what viewing direction and/or in the case of which head movement in the present exemplary embodiment, and what information source should be superimposed/displayed.

In the present exemplary embodiment, the evaluation unit 10 and the actuation unit 11 are realized as software on a computer. The data of the tracking system and the data of the acceleration sensor 9 are transmitted wirelessly to the computer in the process. Likewise, control signals for controlling the degree of transparency of the displays 5A, 5B are transmitted wirelessly from the actuation unit 11 to the displays 5A, 5B. As an alternative to the realization as software on a computer, the evaluation unit 10 and/or the actuation unit 11 can also be integrated into the head-mounted display 1, for example in the form of ASICs (application-specific integrated circuits). If only one of the two units is integrated into the head-mounted display 1 and the other unit is realized as software on a computer, the communication between the unit integrated into the head-mounted display 1 and the unit that is realized as software on a computer is preferably effectuated wirelessly.

Figure 3:
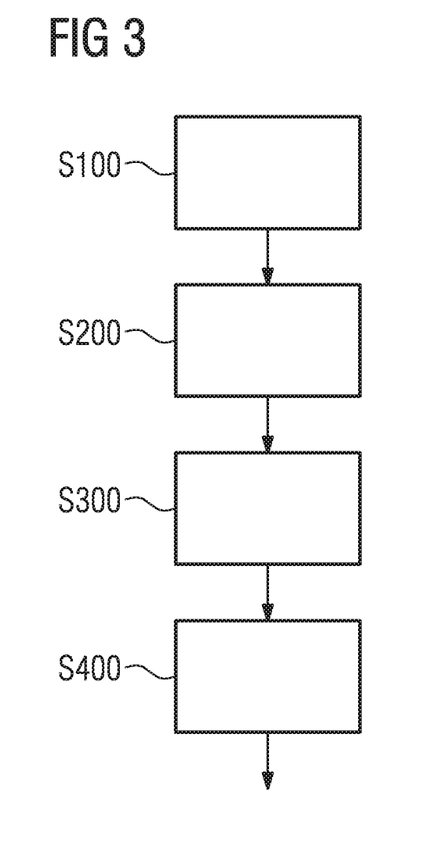
FIG. 3 shows a flowchart of an exemplary embodiment of the method according to the invention.

Now, the operation of the head-mounted display 1 is explained with additional reference to FIG. 3.

A reference direction is set in a first step S100 in the present exemplary embodiment. To this end, the surgeon O can look in the direction of a predetermined reference point, for example. By way of example, a screen, an IR beacon or a marker pointing in the direction of the patient can be used as a reference point. Using this, an information item is provided about the relative position and/or orientation of the coordinate system of the head-wearable presentation apparatus 1 and of a fixed coordinate system, in which the position and orientation of the patient is preferably also set. If the tracking system determines that the viewing direction of the surgeon O is directed in the direction of the reference point, this direction can be set as a reference direction which, for example, may serve for setting right and left in the coordinate system of the surgeon.

Then, orientation data D of the head-mounted display 1 are captured in step S200. In the present exemplary embodiment, acceleration data of the acceleration sensor 9 may also be captured in step S200 in addition to the orientation data D.

Then, in step S300, the captured orientation data D are evaluated in relation to the reference direction in order to determine the viewing direction of the surgeon O. Additionally, it is possible to optionally evaluate the acceleration data in view of a head movement.

Finally, the degree of transparency of the displays 5A, 5B is modified in step S400 if the viewing direction lies in a predetermined direction or, optionally, if a certain head movement is present.

Now, an exemplary assignment of viewing directions to different degrees of transparency is explained with additional reference to FIG. 4.

When the surgeon O looks forward (as illustrated in FIG. 4) within an angular range I, the displays 5A, 5B are opaque, i.e. they have a degree of transparency of 0%. If the surgeon O turns his head 13—and hence his viewing direction—downward, the displays 5A, 5B become fully transparent, i.e. they have a degree of transparency of 100%, for example in order to be able to see instruments. If the surgeon O thereupon turns his head to the right into the angular range II, the displays 5A, 5B remain fully transparent so that the surgeon is able to interact with a theater nurse. Additionally, pre-surgical radiological data may be presented on the displays 5A, 5B. If the surgeon O thereupon turns his view to the left into the angular range III, the displays 5A, 5B likewise remain fully transparent in order to be able to interact with further persons and patient data such as e.g. vital data such as pulse and/or oxygen saturation are optionally presented by superimposition on the displays 5A, 5B. If the view of the surgeon thereafter migrates back to toward the front and straight ahead, i.e. not downward, the displays 5A, 5B become opaque again. Moreover, an image obtained by way of a digital operating microscope, for example, is presented as a VR image. Independently of the viewing direction, the surgeon O can moreover bring about complete transparency of the displays 5A, 5B in the present exemplary embodiment by shaking his head. In contrast, the displays 5A, 5B can be made opaque independently of the viewing direction by nodding of the head 13.

Figure 5:
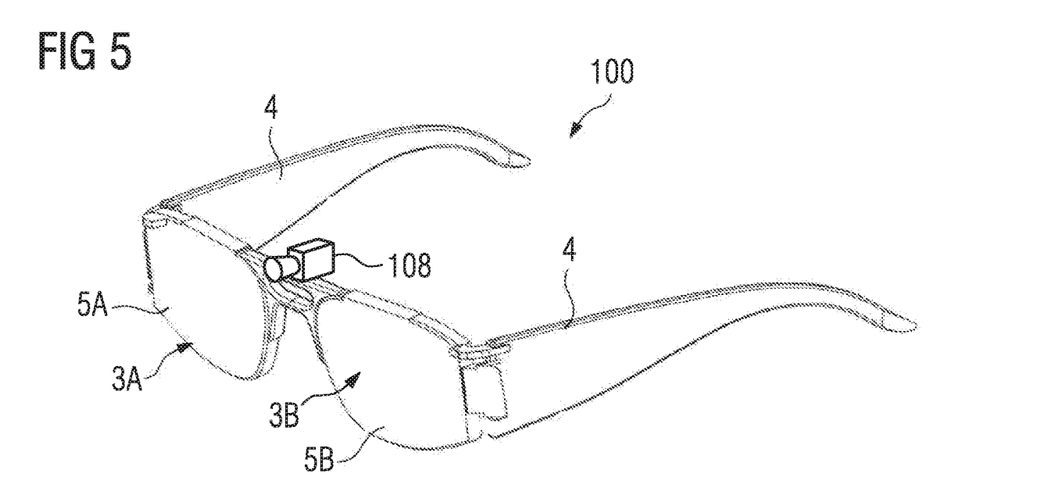
FIG. 5 shows a head-mounted display according to an alternative exemplary embodiment of the head-wearable presentation apparatus.

An alternative exemplary embodiment of the head-mounted display 100 is shown in FIG. 5. The head-mounted display 100 according to the second exemplary embodiment differs from the first exemplary embodiment in the way in which the viewing direction is determined. Instead of the markers 8 or a gyroscopic sensor, a camera 108 is present in the exemplary embodiment illustrated in FIG. 5, said camera being used to record a visual field that corresponds to the orientation of the head 13 of the surgeon O. The evaluation unit 10 evaluates the image data contained in the recording, for example by means of a pattern recognition unit, in order to ascertain predefined image contents. By way of example, these could be certain elements present in the operating theater, for example a suitably positioned ground glass disk or certain appliances that are present in the operating theater. If one or more of these predefined image contents are identified in the image data, the viewing direction of the surgeon can be ascertained from the arrangement of the corresponding elements in the recorded visual field. Alternatively, there is also the option of pursuing a SLAM approach from robotics by means of a white-light camera. Here, SLAM denotes "Simultaneous Localization and Mapping". In the SLAM approach, a map of the surroundings is created incrementally from recordings of the surroundings of the head-mounted display 100, the position and orientation of the head-mounted display 100 being known in said map. It is also possible to use depth sensors such as e.g. TOF cameras as alternatives to conventional cameras in order to create a map of the surroundings, in which the position and orientation of the head-mounted display 100 are known The present invention has been described in detail on the basis of exemplary embodiments for explanation purposes. However, a person skilled in the art recognizes that there may be deviations from the exemplary embodiments within the scope of the present invention. Thus, the head-wearable presentation apparatus can be configured as a loupe instead of as a head-mounted display, it being possible, with an adjustable transparency, to mirror contents that are displayed on at least one display into the magnification beam path by means of a mirror in the case of said loupe. Here, loupes are understood to mean magnifying glasses arranged on a type of spectacle frame. Loupes mainly find use in the fields of medicine and technology. Thus, a loupe is a great advantage for the surgeon for a magnified presentation of the operating region in general, cardiac, and visceral or eye muscle surgery, for example. By switching the transparency of the mirror from transparent to opaque, it is possible to switch back and forth between an AR mode and a VR mode of the superimposition of the contents displayed on the at least one display. Here, as described using the example of the head-mounted display, the degree of transparency can be controlled on the basis of the viewing direction and/or on the basis of head movements. Therefore, the present invention is not intended to be restricted to the described exemplary embodiments, but rather only by the appended claims.

LIST OF REFERENCE SIGNS

1 Head-mounted display
2 Operating microscope
2A, B Image sensors
3A,B Playback arrangement
4 Head sidepiece
5A,B Screen
6 Capture unit
8 Marker
9 Acceleration sensor
10 Evaluation unit
11 Actuation unit
13 Head
100 Head-mounted display
108 Camera
I Angle range
II Angle range
III Angle range
D Data
O Surgeon
S Signal
S100 Setting a reference direction
S200 Capturing orientation data
S300 Evaluating orientation data
S400 Modifying the degree of transparency

The invention claimed is:

1. A method for operating a head-wearable presentation apparatus comprising at least one display device and at least one image capturing device, the method comprising:
receiving image data from the at least one image capturing device, the image data representing a visual field corresponding to an orientation of a head of a subject wearing the head-wearable presentation apparatus;
processing the image data to determine orientation data based on ascertaining one or more predefined image contents within the image data corresponding to real-world objects within real space and the visual field and an arrangement of the one or more predefined image contents;
sending the orientation data to at least one processing device to determine at least one state variable of the subject wearing the head-wearable presentation apparatus; and
modifying a degree of transparency of the at least one display device upon determining the at least one state variable of the subject corresponds to a predetermined state variable,
wherein the one or more predefined image contents comprise one or more elements found in an operating theater, and
wherein the one or more elements found in the operating theater comprise a ground glass screen, one or more appliances, or a combination thereof.

2. The method of claim 1, wherein the orientation data further comprises a position of the subject wearing the head-wearable presentation apparatus.

3. The method of claim 1, wherein the orientation data is determined by first determining reference data based on a reference point in the image data.

4. The method of claim 1, wherein the orientation data comprises movement data and/or acceleration data of the head-wearable presentation apparatus, and wherein the at least one state variable comprises head movement of the subject wearing the head-wearable presentation apparatus.

5. The method of claim 1, wherein the at least one processing device is located on the head-wearable presentation apparatus.

6. The method of claim 1, wherein the at least one processing device is remote to the head-wearable presentation apparatus.

7. The method of claim 1, wherein the at least one image capturing device is a camera mounted to the head-wearable presentation apparatus.

8. A non-transitory computer-readable storage medium storing at least one program configured to be executed by at least one processor at a computer comprising instructions for:
- receiving image data from at least one image capturing device, the image data representing a visual field corresponding to an orientation of a head of a subject wearing a head-wearable presentation apparatus;
- processing the image data to determine orientation data based on ascertaining one or more predefined image contents within the image data corresponding to real-world objects within real space and the visual field and an arrangement of the one or more predefined image contents;
- determining at least one state variable of the subject wearing the head-wearable presentation apparatus based on the orientation data; and
- modifying a degree of transparency of at least one display device upon determining the at least one state variable of the subject corresponds to a predetermined state variable,
- wherein the one or more predefined image contents comprise one or more elements found in an operating theater, and
- wherein the one or more elements found in the operating theater comprise a ground glass screen, one or more appliances, or a combination thereof.

9. The non-transitory computer-readable storage medium of claim 8, wherein the orientation data further comprises a position of the subject wearing the head-wearable presentation apparatus.

10. The non-transitory computer-readable storage medium of claim 8, wherein the orientation data is determined based on reference data determined by a reference point in the image data.

11. The non-transitory computer-readable storage medium of claim 8, wherein the orientation data comprises movement data and/or acceleration data of the head-wearable presentation apparatus, and wherein the at least one state variable of the head comprises head movement of the subject wearing the head-wearable presentation apparatus.

12. The non-transitory computer-readable storage medium of claim 8, wherein the at least one image capturing device is a camera mounted to the head-wearable presentation apparatus.

13. A head-wearable presentation apparatus comprising:
- at least one image capturing device configured to capture image data, the image data representing a visual field corresponding to an orientation of a head of a subject wearing the head-wearable presentation apparatus;
- at least one processing device configured to:
  (1) process the image data to determine orientation data based on ascertaining one or more predefined image contents within the image data corresponding to real-world objects within real space and the visual field and an arrangement of the one or more predefined image contents; and
  (2) determine at least one state variable of the subject wearing the head-wearable presentation apparatus based on the orientation data; and
- at least two display devices configured to be modified with respect to a degree of transparency based upon determining the at least one state variable of the subject corresponds to a predetermined state variable,
- wherein the one or more predefined image contents comprise one or more elements found in an operating theater, and
- wherein the one or more elements found in the operating theater comprise a ground glass screen, one or more appliances, or a combination thereof.

14. The head-wearable presentation apparatus of claim 13, wherein the orientation data further comprises a position of the subject wearing the head-wearable presentation apparatus.

15. The head-wearable presentation apparatus of claim 13, wherein the orientation data is determined based on reference data determined by a reference point in the image data.

16. The head-wearable presentation apparatus of claim 13, wherein the orientation data comprises movement data and/or acceleration data of the head-wearable presentation apparatus, and wherein the at least one state variable comprises head movement of the subject wearing the head-wearable presentation apparatus.

17. The head-wearable presentation apparatus of claim 13, further comprising at least one image capturing device mounted on the head-wearable presentation apparatus configured to provide image data,
- wherein the orientation data comprises a viewing direction of the subject wearing the head-wearable presentation apparatus determined using the image data received,
- wherein the viewing direction is determined by identifying a predetermined image content within the image data received.

* * * * *